United States Patent

Solomons et al.

[11] 4,256,839
[45] Mar. 17, 1981

[54] REACTOR SYSTEM SUCH AS A FERMENTATION SYSTEM

[75] Inventors: Gerald L. Solomons, Radnage; Geoffrey A. LeGrys, Oxon, both of England

[73] Assignee: Ranks Hovis McDougall Limited, London, England

[21] Appl. No.: 911,125

[22] Filed: May 31, 1978

[30] Foreign Application Priority Data

Jun. 1, 1977 [GB] United Kingdom ............... 23128/77

[51] Int. Cl.³ .......................... C12M 1/08; C12M 1/06
[52] U.S. Cl. ...................................... 435/314; 366/295
[58] Field of Search ............... 195/139, 142, 143, 109; 366/292-295; 435/314, 315

[56] References Cited

U.S. PATENT DOCUMENTS

| | | | |
|---|---|---|---|
| 1,598,185 | 8/1926 | Willard | 366/294 X |
| 2,438,204 | 3/1948 | Castner | 366/293 X |
| 2,615,697 | 10/1952 | Valentine | 366/293 X |
| 3,236,744 | 2/1966 | Yamaha | 195/143 |
| 3,954,565 | 5/1976 | Boiko et al. | 195/139 X |
| 3,962,042 | 6/1976 | Malick | 195/143 |

FOREIGN PATENT DOCUMENTS 10154 of 1914 United Kingdom ..................... 366/295

Primary Examiner—Robert A. Yoncoskie
Attorney, Agent, or Firm—McCormick, Paulding & Huber

[57] ABSTRACT

An apparatus for effecting mass transfer in fermentation reactions is disclosed. The apparatus includes a cylindrical vessel with two impellers located toward the top and bottom of said vessel, one of which is an axial flow impeller and the other is a radial flow impeller. A draft tube of uniform diameter throughout substantially all of its length having an open bottom is located within and coaxial with said cylindrical vessel. The lower impeller being said radial flow impeller is located below the lower end of the draft tube.

5 Claims, 7 Drawing Figures

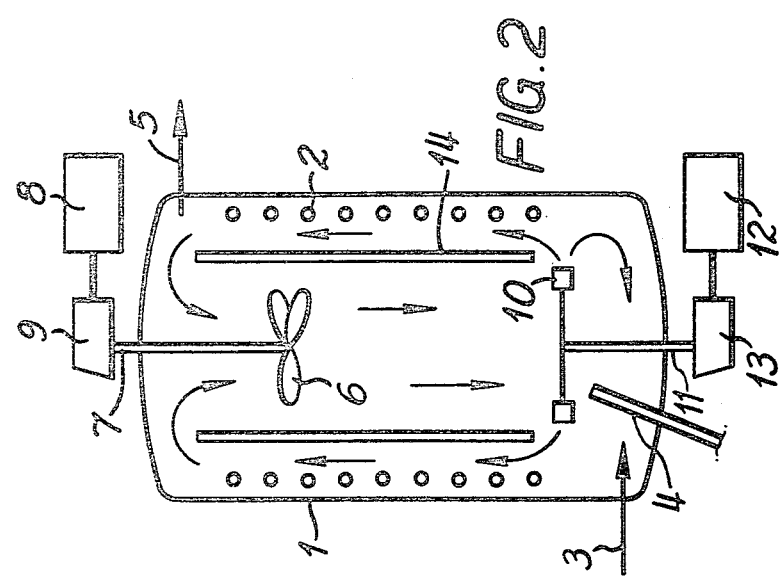
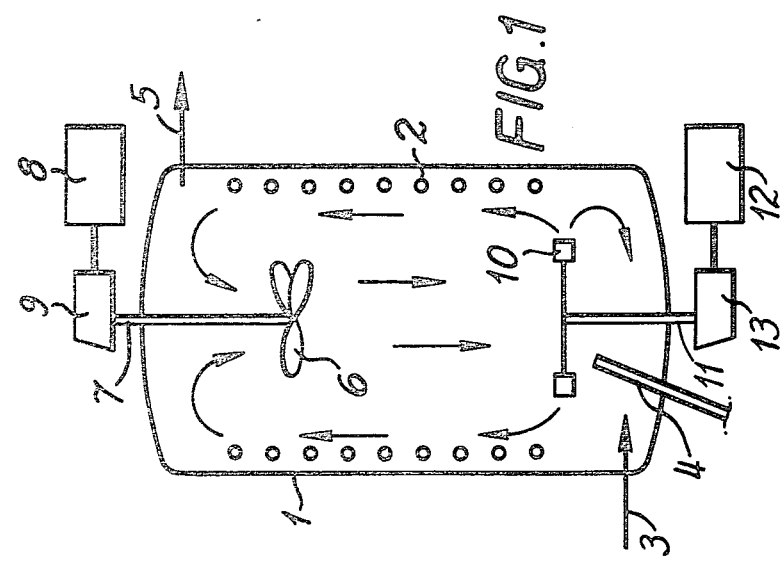

REACTOR SYSTEM SUCH AS A FERMENTATION SYSTEM

TECHNICAL FIELD

The invention is concerned in its broadest aspect with any reactor system involving the dissolution of a sparingly soluble gas or liquid or solid material within a large body of liquid. More specifically, the invention is concerned with aerobic fermentation, for example, the production of micro-organisms as a source of non-toxic foodstuffs suitable for animal or human use or for the production of antibiotics, citric acid or steroid hormone conversion.

BACKGROUND ART

Mycelial fungi grown under controlled conditions in a fermenter are a source of protein and therefore useful as a foodstuff. Non-toxic fungal mycelium, particularly suitable as a foodstuff for humans, are disclosed in United Kingdom Pat. Specs. Nos. 1,331,472 and 1,346,062. The preferred non-toxic fungal mycelium is Fusarium graminearum Schwabe I.M.I. No. 145,425. Mechanically agitated aerobic fermenters are suitable for the growing of the biomass and currently known fermenters having mechanical agitation either have a single impeller or a series of impellers mounted on a single shaft for circulating the mass within the fermenter. The fermenter shell is normally cylindrical in shape with the axis of the cylinder vertical and if more than one impeller is provided, they are disposed along the axis of the fermenter. It has been previously proposed to provide two such impellers, one towards the top of the fermenter and one towards the bottom although it is well known that two radial flow impellers will set up two separate regions around each impeller with very little mixing between these regions.

A fermenter is designed to supply a suiable environment for the culture and nourishment of the micro-organism being grown. In the prior art, cultures of yeast and bacteria have been grown aerobically in fermenters and such cultures generally have a low viscosity of the order of water. In comparison, a filamentous mycelial mass such as the preferred micro-organism mentioned above has a much higher viscosity, and is usually non-newtonian. This high viscosity has an adverse effect on the mixing in the fermenter which is necessary for the fungal mycelia to experience a uniform environment. In the case of our preferred micro-organism, 1 gram of mycelia is produced for every 2 grams of glucose, 0.78 grams of oxygen and 0.1 gram of ammonia consumed. Unlike glucose and to a certain extent ammonia which have high solubility in aqueous systems, oxygen has a very low solubility. For example, at 30° C. and at one atmosphere pressure, oxygen has an equilibrium solubility of 0.007 to 0.008 grams per liter depending on the concentration of salts. If at any instant, the system is saturated with oxygen in equilibrium with air, a micro-organism obeying the above stoichiometry at a vessel productivity of 3 grams per liter per hour, will utilize all the dissolved oxygen in 10.8 seconds. This time can be increased to 25.5 seconds using air by increasing the pressure to 20 p.s.i.g. An equivalent increase in this time can be achieved at atmospheric pressure by supplying oxygen enriched air, which has a partial pressure of oxygen at atmospheric pressure, equal to the partial pressure of the oxygen in air at 20 p.s.i.g. Prior art fermenters have not proved to be entirely satisfactory for maintaining adequate dissolved oxygen in this period.

DISCLOSURE OF INVENTION

It has now been found that a fermenter having two impellers, wherein these two impellers serve totally different functions during the operation of the fermenter, can achieve the desired distribution of air and recirculation of the biomass to optimise oxygen transfer. The nutrients are normally fed into the lower part of the fermenter in the region of the lower impeller and, in order to promote the growth of the biomass, the oxygen is fed into the lower or upper parts of the fermenter or both and should be broken up so that it forms a fine dispersion. The oxygen available to the cells is mainly concentrated in the region of the impeller(s). For an efficient operation of the fermenter it is necessary for the cells to return to the oxygen-rich region of the fermenter within a specified period of time dependent upon the oxygen utilisation rate of the biomass and this is achieved by circulating the biomass throughout the vessel. It is the function of the upper impeller to circulate the biomass at such a rate that an adequate supply of oxygen will be presented to the cells and to ensure as far as possible that no stagnant regions occur within the fermenter. These criteria cannot adequately be satisfied by existing fermenter design and therefore it is the main object of this invention to provide a construction of fermenter with improved operating efficiency.

It is a further object of this invention to provide a vessel within which a mass transfer process may occur under controlled conditions.

According to the present invention there is provided a method of promoting fermentation in the production of a biological product, in which nutrients including oxygen are added to a biomass or ferment in a fermenter the fermenter having two impellers which are driven at different speeds, one impeller mainly achieving circulation of the biomass or ferment within the fermenter and the other impeller mainly creating a fine dispersion of the oxygen. The invention also includes the method as above applicable to the production of a mycelial fungal mass in which substantially all of the cells within the biomass achieve complete circulation within the fermenter within 10 to 30 seconds.

The invention further includes a vessel for effecting mass transfer having two impellers, means for rotating the impellers and means for separately controlling the speeds of rotation of the impellers.

The vessel may be a fermenter which is cylindrical with its axis vertical and the impellers disposed along said axis, one towards the top of the fermenter and the other towards the bottom of the fermenter, the one impeller being an axial uniform flow impeller to produce a downward flow near the axis of the fermenter and the other impeller being a disc turbine to produce a radially outward flow.

Preferably, the diameter of the top impeller is 0.5 to 0.6 the internal diameter of the fermenter. The said top impeller may be a sabre blade impeller having three thin section blades shaped to give a uniform displacement flow across its diameter.

A draught tube may also be located within and coaxial with the fermenter, the said tube being substantially 0.7 of the fermenter diameter.

Typically, the bottom impeller is a disc turbine having a diameter of 0.2 to 0.5 the internal diameter of the fermenter. Preferably, the turbine impeller has a diameter of 0.2 to 0.3 the diameter of the fermenter.

BRIEF DESCRIPTION OF DRAWINGS

Three embodiments of fermenter constructed in accordance with the invention will now be described, by way of example only, and with reference to the accompanying drawings, in which:

FIG. 1 is a diagrammatic representation of one construction of fermenter according to the invention;

FIG. 2 is a diagrammatic representation of a modified form of fermenter according to the invention;

BEST MODES FOR CARRYING OUT THE INVENTION

Figure 3:
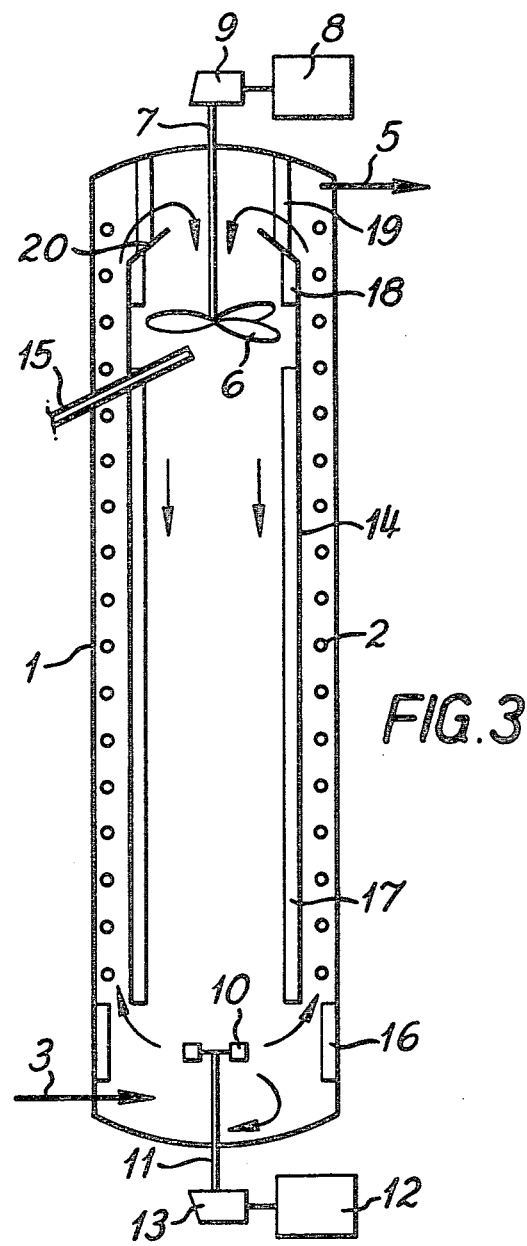
FIG. 3 is a diagrammatic representation of a further form of fermenter according to the invention.

Referring first to FIG. 1 a fermenter shell 1 is cylindrical with heat transfer coils 2 mounted within. Means is provided at 3 for the inlet of nutrients including the introduction of sparge air at 4 for the supply of oxygen to the cells. Cells are removed from the fermenter at 5.

Disposed towards the top of the fermenter and coaxially therewith is an impeller 6 driven by a shaft 7 from any suitable type of power source 8 through gearing 9. This gearing 9 includes means whereby the speed of rotation of the impeller 6 may be independently varied.

The main function of this upper impeller 6 is to provide for the circulation of the biomass around the fermenter as indicated by the flow arrows in FIG. 1. Preferably, the impeller 6 gives uniform flow characteristics so that substantially all of the biomass within the fermenter will circulate through the fermenter with a common circulation time. Any impeller which achieves this end is suitable as the impeller 6 and a sabre blade impeller has been found particularly suitable. This impeller 6 is of large diameter, preferably 0.5 to 0.6 the diameter of the fermenter and will operate at comparatively low speeds. It should operate at such a speed that the entire biomass will circulate through the fermenter every 10 to 30 seconds.

The lower impeller 10 is located coaxially with the axis of the fermenter 1 and is driven by shaft 11 from power source 12 through gearing 13. The gearing 13 includes means for infinitely varying speed of rotation of impeller 10. In a large fermenter the impeller 10 may have a fixed speed. The diameter of the impeller 10 should be in the range of 0.2 to 0.5 and preferably 0.2 to 0.3 the diameter of the fermenter 1 and a disc turbine producing a radially outward flow has been found particularly suitable. This impeller 10 creates a fine dispersion of the air injected at 4 and also assists in the circulation of the biomass throughout the fermenter.

The FIG. 2 embodiment is simply a modification of that of FIG. 1 and like parts have been given like reference characters. In the FIG. 2 embodiment, a draught tube 14 has been located within the fermenter 1. This draught tube 14 is cylindrical and has a diameter approximately 0.7 the diameter of the fermenter and a height approximately 1.5 the diameter of the fermenter.

This draught tube 14 assists in the separation of the upward and downward flows of the biomass during the circulation. The cross-sectional area taken in a horizontal plane within the draught tube 14 should be equal to the cross-sectional area in a horizontal plane between the draught tube and the fermenter shell.

Preferably, the upper impeller 6 lies within the draught tube 14 and the lower impeller 10 lies outside it. Also, the upper impeller may be positioned about one diameter of the impeller from the top of the fermenter and the lower turbine about one turbine diameter from the bottom of the fermenter.

The turbine serves to increase the rate at which oxygen transfer occurs by forming a dispersion of small air bubbles with large interfacial area. In the region near the turbine impeller it is possible to achieve near equilibrium between the concentraton of the oxygen in the fermenter broth and the partial pressure of oxygen in the air bubbles. As the air bubbles are moved away from the turbine impeller by hydro-dynamic forces, the rate of oxygen transfer decreases rapidly as the air bubbles are no longer situated in a highly turbulent region. Turbulence improves mass transfer because it induces surface renewal and movement at the gas-liquid interface.

A further modification to the construction described above may be made within the scope of the present invention. This allows for the limitation that occurs in large fermentation systems of insufficient cooling capacity to remove the metabolic heat. A simple explanation of this phenomena is, as is well known by those skilled in the art, that the amount of metabolic heat increases as the cube of the vessel diameter while the area available to cool the vessel contents increases only as the square of the vessel diameter.

An example of this scale effect on heat transfer can be seen by consideration of the area available for cooling in some specific examples.

In the cases under consideration the cooling could be achieved by a double bank of internal coils constructed with 3 inch diameter pipe. The pipe is on a 6″ spiral pitch with the pitch circle diameter s of the two coils respectively 1 ft and 2 ft less than the vessel diameter. Hemicoils on the vessel shell spaced at 6″ intervals are also included.

With this cooling surface arrangement one can estimate the amount of cooling surface per unit volume of vessel.

This gives case 1–3 in the following table (Case 4 is geometrically similar to case 3 but one third the diameter)

| CASE | VOLUME (FT$^3$) | DIAMETER (FT) | H:D | COOLING COILS | AREA (FT$^2$) SHELL | COOLING SURFACE/ VESSEL VOLUME (FT$^{-1}$) |
|---|---|---|---|---|---|---|
| 1 | 6,400 | 16 | 2:1 | 4295 | 804 | 0.80 |
| 2 | 12,600 | 20 | 2:1 | 6940 | 1256 | 0.65 |
| 3 | 12,850 | 16 | 4:1 | 8875 | 1608 | 0.82 |
| 4 | 475 | 5′4″ | 4:1 | 986 | 178 | 2.45 |

Cases 2 and 3 show that the cooling surface/unit volume that could be fabricated inside similar volume vessels is some 25% higher in a 16 ft diameter vessel (H:D=4:1) compared to a 20 ft vessel (H:D=2:1). This would show a corresponding reduction in coolant requirements.

Comparison of cases 3 and 4 exemplify the scale effect. Thus, cooling which is relatively easy on small and pilot plant vessels, becomes increasingly difficult as the size of the vessel increases. One can of course change from say cooling tower water to refrigerant but the cooling medium, then, becomes increasingly expensive.

A practical maximum diameter is therefore established. The actual value of this maximum will depend on geographical location, source of cooling water but will generally be about 16 ft.

This diameter also has other consequences as it is about the maximum diameter load that can be freely transported by road in many countries. This would allow the vessel to be fabricated off-site with a subsequent saving of costs.

A vessel constructed to this diameter would to achieve a given fermentative capacity, have to be increased in height. Depending upon the rheological properties of the culture broth the ratio of height to diameter could be increased subject to the limitation that the pressure developed by the axial flow impeller is sufficient to overcome the frictional resistance on the draft tubes and the vessel wall.

A representation of an arrangement of a vessel conforming to these ideas is given in FIG. 3. In this case the vessel has a height to diameter ratio of approximately 4:1 and the gas is sparged either through a single port or a multiple port in the region of impeller 6 throughout the sparger 15.

Besides the internal features discussed with the embodiments of FIGS. 1 and 2, the arrangement in the FIG. 3 embodiment has several other additional features. The vessel has several baffles 16, 17 and 18 to inhibit swirling motion. These are, as in prior art, located near the turbine impeller but it would also be possible to baffle the inside of the draft tube and the region above the draft tube at 19. The baffles would in general conform to current design art.

The top of the draft tube could be partially enclosed by a truncated cone or similar shaped device 20. This would by slowing the fluid velocity in that region, assist the detrainment of the spent gas from the fermentation broth.

In view of the limitations of specific area available for heat transfer and the ease of fabrication and transport it is desirable to limit the diameter of the fermenter to not greater than 16 feet. To obtain the same fermenter capacity it would be necessary to increase the height of the vessel which would have the added benefit of increased solubility of oxygen near the turbine impeller. The benefit of sparging at the top of the vessel, would in terms of compressor size and power requirements, be considerable.

As an example consider a vessel volume 80,250 gallons (12,870 ft$^3$) which is 16 feet diameter and 64 feet high. Operating this with a 12 bladed disc turbine 4 feet diameter rotating at 170 rpm, would given an absorbed power of 800 hp (1 hp/100 gall), although it is expected that equivalent performance could be achieved with a total absorbed power somewhat less than 800 hp. As an example, the viscosity of a non-newtonian mycelial fermentation broth corresponding to this rotational speed is 0.117 lb/ft/sec and the resulting volumetric flow from this turbine would be 120 ft$^3$/sec. Thus this turbine operating alone would result in an average circulation time of 107 seconds, a time well outside our design criterion for the respiration of the fermenting organism. An impeller 11 feet diameter operating at 60 rpm would absorb only 60 hp and would give a volumetric flow within the fermenter of 460 ft$^3$/sec. Thus the average circulation time of th sabre/turbine combination would be 22 sec.

The benefit of sparging the gas at the top of the vessel can be appreciated by calculating the hp requirements of the compressor allowing 5 psig overpressure for passage through fixture and fittings.

Head of liquid sparged at turbine = 56 ft = 25 psig
Head of liquid sparged at sabre = 16 ft = 7 psig
Sparging the above vessel with 6,400 standard cubic feet/minute (0.5 volume/volume/minute) would, by calculating a theoretical horsepower, required 740 hp and 360 hp respectively.

The positioning of the sparger and the effectiveness of the axial flow device can be demonstrated by the following data which was obtained in a 40 liter mixing vessel conforming to the present invention. In each case the measurement is the volumetric mass transfer coefficient ($k_La$) which, those skilled in the art will recognise, is a measure of the efficiency of the vessel to transfer oxygen from the gas phase to the liquid phase.

Figure 4:
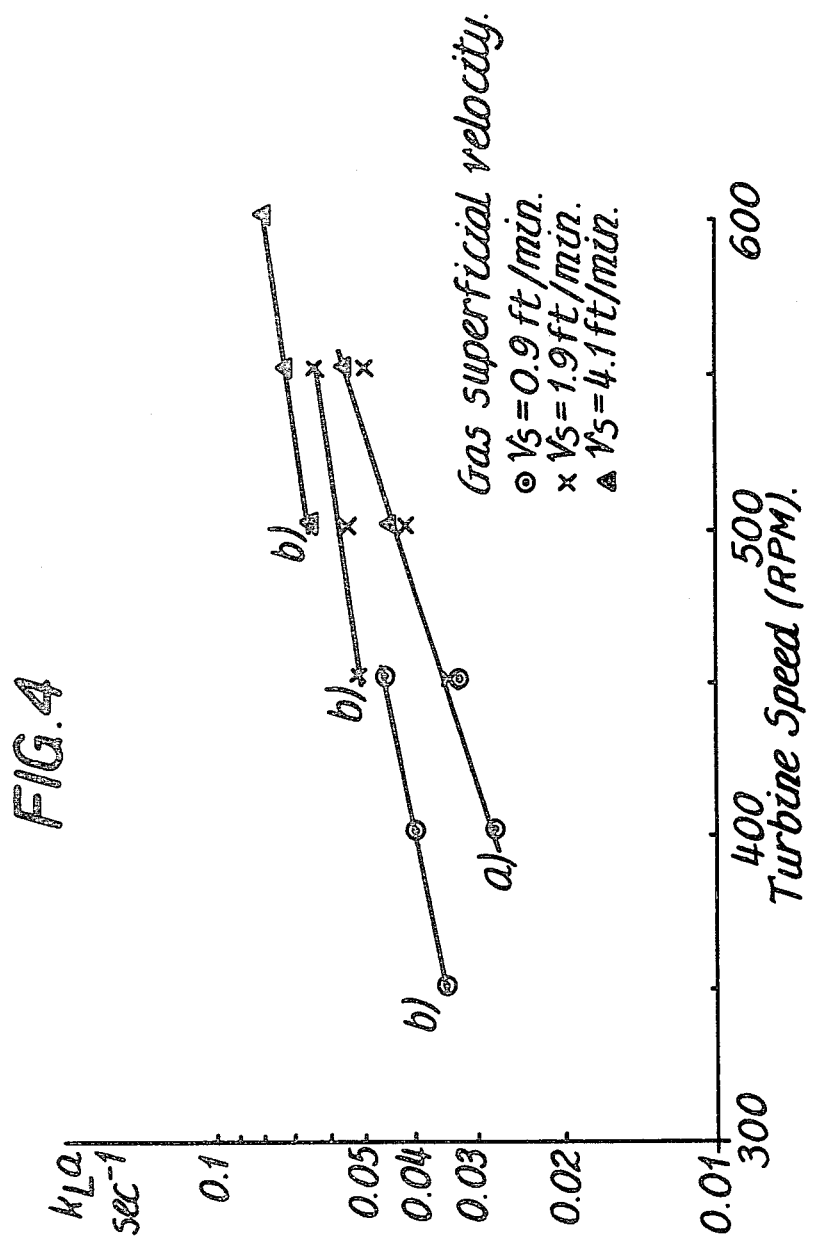
FIG. 4 is a graph giving a measure of the efficiency of a fermenter to transfer oxygen from the gas phase to the liquid phase at various turbine speeds.

FIG. 4 shows the value of $k_La$ at several gas flow rates when the gas is introduced at the sabre region (a) and at the turbine region (b); in both cases the sabre is not operating and therefore not pumping the gases and liquid around the vessel. This is particularly relevant for the gases in case (a). The fluid is water corresponding to inviscid fermentation systems. It is seen that when the gas is introduced at the top of the vessel the $k_La$ is considerably reduced; changing the gas flow rate has little effect. These results are consistent with little circulation of the gas. Sparging at the bottom without the sabre operating (b) corresponds to current practice. It is concluded from these examples that it is necessary when sparging gas at the top of the vessel that some flow inducer is necessary to pump the gas and liquid around the vessel.

Figure 5:
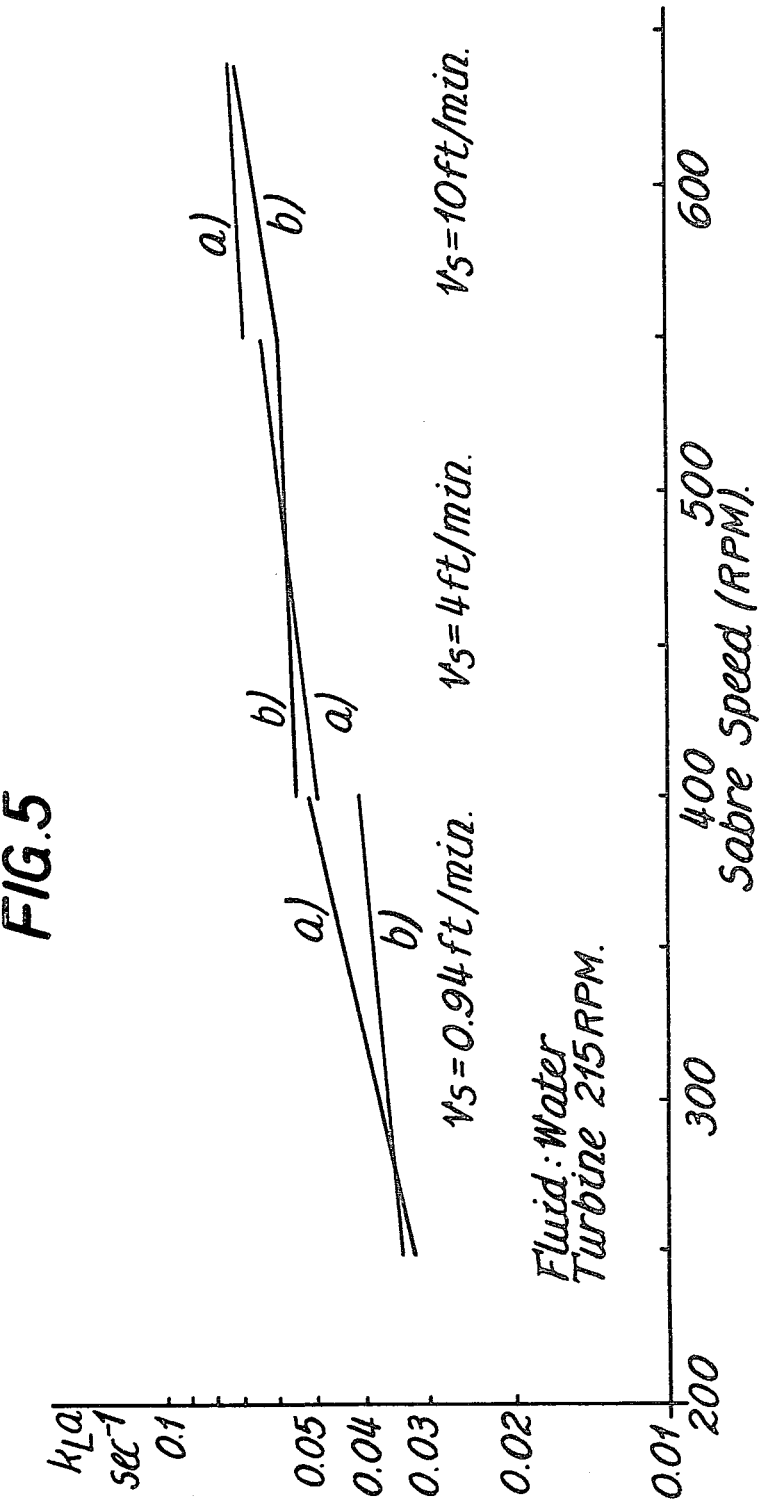
FIG. 5 is a graph giving a measure of the efficiency of a fermenter to transfer oxygen from the gas to the liquid phase at various sabre speeds.

The effect of operating the sabre can be judged from FIG. 5. In these cases the turbine is operating at 215 rpm. Cases (a) correspond to sparging at the sabre region, (b) to the turbine region. In these two instances it is seen that little or no sensible difference between performance, as measured by the $k_La$'s when the vessel is sparged at the sabre (a) or at the turbine (b) with the other operating conditions equivalent. Thus, equivalent performance would be expected with the relevant saving in compressor hp which in large vessels would be considerable.

Figure 6:
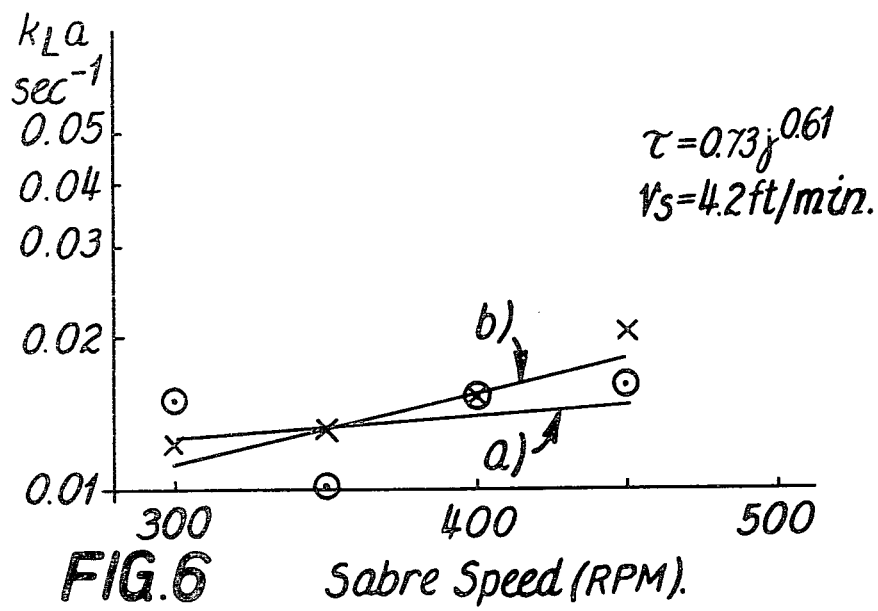
FIGS. 6 and 7 are further graphs showing performances when the test fluid is a fermentation broth.
Figure 7:
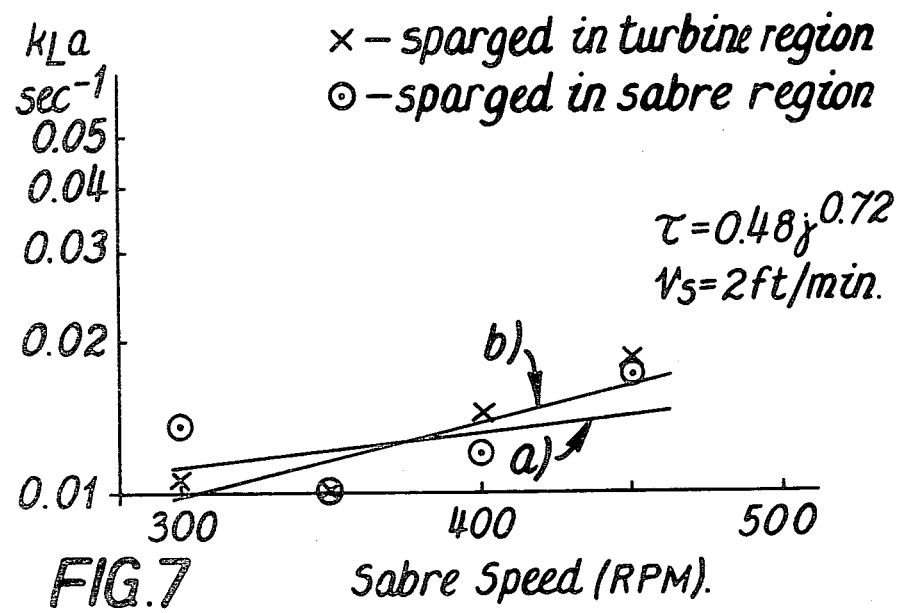

These general conclusions are reproduced when the test fluid is a fermentation broth exhibiting viscous non-newtonian behaviour. In FIGS. 6 and 7 the performance of a 40 liter vessel with air sparged near the sabre (a) is compared with air sparged near the turbine (b). In both cases the turbine is rotated at 215 rpm. The broth's rheological behaviour is in the two cases considered in FIGS. 6 and 7 is described, respectively by the following equations:

$$\tau = 0.73 j^{0.61}$$

and $$\tau = 0.48 j^{0.72}$$

Those skilled in the art will recognise these as a relationship between shear stress (τ) in poundals/ft² and shear rate (j) in sec⁻¹ that demonstrates considerable pseudo-plasticity.

In both FIGS. 6 and 7 it is seen that, other operating parameters being equal, that $k_La$ values are roughly equivalent when the vessel is sparged in the sabre region as compared with the vessel sparged in the turbine region. Thus again we have equivalent performance with a saving in compressor hp which in large vessel would be considerable.

It is to be understood that the present invention finds use in supplying any gas of limited solubility to a fermenter broth and is not limited to oxygen. The mass transfer of gas to fermenter broth is reduced in viscous systems typical of mycelial fermentations as there is a tendency for the air bubbles rapidly to coalesce which results in a reduction of total inter-facial area and attendant mass transfer. The present invention also finds use in supplying liquid or solid nutrients or additives to a fermenter broth in applications wherein such liquid or solid nutrient or additives have limited solubility in the fermenter broth.

While the present invention is particularly useful in the fermentation of mycelia, it also is applicable in the fermentation of yeasts and bacteria when it is desired to use large fermenters. This is because even though such yeast and bacteria ferments are not as viscous as mycelial ferments and therefore are more amenable to mixing in a large conventionally stirred fermenter the energy input necessary to circulate the ferment back to a given supply point within a time period necessary to maintain a uniform environment, rapidly becomes excessive as the size of the fermenter is scaled up.

In the present invention the two impellers are operated independently and generally at quite different speeds. This results in a considerable energy saving. For instance, in the case of a 1270 liter fermenter containing a ferment having a viscosity of 0.096 lb/ft sec., a top mounted 2.0 ft diameter sabre impeller driven at 30 rpm and a bottom mounted 1.0 ft diameter twelve blade disc turbine driven at 260 rpm, the circulation time is 10.6 sec. and the power input is 2.9 hp. In the case of the same 1270 liter fermenter containing a ferment having a viscosity of only 0.085 lb/ft/sec., when the sabre is driven at 30 rpm and the turbine is driven at 325 rpm the circulation time is 8.9 sec., and the power input is 5.7 hp. This second case can be modified considering the turbine agitating the ferment alone. The circulation time due to the pumping action of the turbine alone is increased to 13.8 seconds saving in power uptake of 0.1 h.p. of the sabre impeller.

The power saving improvement in circulation time by the present invention is considerable for large vessels. For instance in the case of a 152,000 Imperial gallon fermenter containing a ferment having a viscosity of 0.166 lb/ft/sec a top mounted 16¼ft diameter sabre impeller driven at 17 rpm and a bottom mounted 6.5 ft diameter twelve bladed disc turbine driven at 86 rpm, the circulation time is 20.2 secs and a power input of 1216 hp. If the turbine is agitating the fermenter alone the circulation time is increased to 102 secs. saving only 105 hp. Thus it is apparent from these cases that the present invention achieves considerable power saving in an equivalent fermentation while achieving equivalent results.

Also because only two comparatively short drive shafts are necessary, instead of a single long shaft in prior art arrangements, the cost of construction will be reduced.

Various modifications to the constructions described above may be made within the scope of the present invention. For example, sparge air may be introduced from the top of the fermenter as an alternative to sparging in the region of the lower impeller. This would reduce the energy required to push the air bubbles around the fermenter. The down velocity of the fluid exceeding the terminal rise velocity of the air, the air sparger would consequently be run using a cheaper compressor leading to a reduction in costs.

Also the construction may be modified when the biomass is hyphal in character in that to induce greater growth the lower impeller may be provided with flails or other mechanical breakers to thrash and break the hyphal cells. Alternatively or additionally areas of high shear may be created in the base of the fermenter by the provision, under the lower impeller of a plurality of small subsidiary impellers. These subsidiary impellers would have the effect of breaking down the hyphae and thereby inducing hyphal regeneration.

We claim:

1. An apparatus for effecting mass transfer, said apparatus comprising a vessel which is cylindrical and arranged with its axis vertical, two impellers located in said vessel for rotation about vertical axes generally aligned with the vertical axis of said vessel, one of said impellers being located toward the top of said vessel and the other of said impellers being located toward the bottom of said vessel, one of said impellers being an axial flow impeller to produce a flow along the axis of said vessel and the other of said impellers being a radial flow impeller to produce a radially outward flow therefrom, and said radial flow impeller and said vessel being so related that a structure free annular zone exists between the outer periphery of said radial flow impeller and the cylindrical wall of said vessel to permit material to flow unimpeded from said radial flow impeller toward said cylindrical wall of said vessel, and a draft tube located within and generally coaxial with said cylindrical vessel, said draft tube being of a uniform diameter throughout substantially all of its length and having an open bottom of said uniform diameter, said lower impeller being said radial flow impeller and being located below said lower end of said draft tube.

2. An apparatus as defined in claim 1 further characterized by said axial flow impeller being located within the upper portion of said draft tube.

3. An apparatus as defined in claim 2 further characterized by said axial flow impeller having a diameter which is between 0.5 to 0.6 of the internal diameter of said vessel, and said uniform diameter of said draft tube being approximately 0.7 of the internal diameter of said vessel.

4. An apparatus as defined in claim 1 or claim 2 further characterized by the upper end of said draft tube being partially closed to slow down the fluid velocity in that region.

5. An apparatus as defined in claim 1 or claim 2 further characterized by said draft tube having a partial closure means at its upper end in the form of a truncated cone giving said draft tube an upper opening of a diameter smaller than said uniform diameter, the remainder of said draft tube located below said partial closure means being of said uniform diameter throughout its entire length.

* * * * *